United States Patent
Shi et al.

(10) Patent No.: US 12,310,668 B2
(45) Date of Patent: May 27, 2025

(54) INTELLIGENT PLANNING METHOD, DEVICE, EQUIPMENT AND MEDIUM FOR PUNCTURE PATH IN PVP SURGERY

(71) Applicants: THE FIRST MEDICAL CENTER OF PEOPLE'S LIBERATION ARMY GENERAL HOSPITAL, Beijing (CN); BEIJING ZOEZEN ROBOT CO., LTD, Beijing (CN)

(72) Inventors: Bin Shi, Beijing (CN); Lihai Zhang, Beijing (CN); Yonghong Zhang, Beijing (CN); Lei Hu, Beijing (CN)

(73) Assignees: THE FIRST MEDICAL CENTER OF PEOPLE'S LIBERATION ARMY GENERAL HOSPITAL, Beijing (CN); BEIJING ZOEZEN ROBOT CO., LTD, Beijing (CN)

( * ) Notice: Subject to any disclaimer, the term of this patent is extended or adjusted under 35 U.S.C. 154(b) by 0 days.

(21) Appl. No.: 18/743,167

(22) Filed: Jun. 14, 2024

(65) Prior Publication Data

US 2024/0415576 A1    Dec. 19, 2024

(30) Foreign Application Priority Data

Jun. 15, 2023    (CN) .......................... 202310705522.0

(51) Int. Cl.
*A61B 34/10* (2016.01)
*A61B 17/88* (2006.01)
*A61B 90/00* (2016.01)

(52) U.S. Cl.
CPC .......... *A61B 34/10* (2016.02); *A61B 17/8811* (2013.01); *A61B 90/37* (2016.02); *A61B 2034/107* (2016.02); *A61B 2090/3762* (2016.02)

(58) Field of Classification Search
None
See application file for complete search history.

(56) References Cited

U.S. PATENT DOCUMENTS

2005/0182317 A1    8/2005    Haddad
2006/0235338 A1    10/2006    Pacheco
(Continued)

FOREIGN PATENT DOCUMENTS

CN    204049825 U    12/2014
CN    106420054 A    2/2017
(Continued)

OTHER PUBLICATIONS

Notice of Allowance of counterpart Chinese Patent Application No. 202310705522.0 issued on Dec. 15, 2023.
(Continued)

*Primary Examiner* — Patricia J Park

(57) ABSTRACT

An intelligent puncture path planning method, a device, an equipment and a medium in a PVP operation. The method includes: intercepting a local CT image of a vertebral body from an image; identifying midpoint of the narrowest part of vertebral pedicle and a theoretical puncture injection stop-point from the local CT image through trained neural network model; calculating distance from the stop-point to the middle plane in front-back direction of the vertebral body, distance from the stop-point to the middle plane in left-right direction of the vertebral body and the closest distance from the stop-point to the cortical bone surface, taking the minimum value of distances as radius of a space sphere area with the stop-point as sphere center; taking a line connecting midpoint of the narrowest part of any vertebral pedicle and any point in the space sphere area as an optional puncture path of the vertebral pedicle.

9 Claims, 10 Drawing Sheets

(56) References Cited

U.S. PATENT DOCUMENTS

| | | | |
|---|---|---|---|
| 2009/0131950 A1 | 5/2009 | Liu et al. | |
| 2019/0307410 A1 | 10/2019 | Morita et al. | |
| 2022/0237817 A1* | 7/2022 | Dorman | A61B 90/361 |
| 2023/0177696 A1 | 6/2023 | Qin et al. | |
| 2023/0363822 A1* | 11/2023 | Weede | A61B 90/36 |

FOREIGN PATENT DOCUMENTS

| | | |
|---|---|---|
| CN | 107157579 A | 9/2017 |
| CN | 108784831 A | 11/2018 |
| CN | 212281560 U | 1/2021 |
| CN | 113907879 A | 1/2022 |
| CN | 114145835 A | 3/2022 |
| CN | 115429409 A | 12/2022 |
| CN | 115568943 A | 1/2023 |
| CN | 115984536 A | 4/2023 |
| CN | 116228796 A | 6/2023 |
| JP | 2007054397 A | 3/2007 |
| KR | 1020160010092 A | 1/2016 |
| WO | 2012052929 A2 | 4/2012 |

OTHER PUBLICATIONS

First Office Action of counterpart Chinese Patent Application No. 202310705522.0 issued on Oct. 16, 2023.

Yanchun Xie et al., Application of preoperative accurate plan of puncture path in vertebroplasty, Trauma and Critical Care Medicine, Jul. 15, 2020, pp. 219-223 and 227, vol. 8, No. 4.

Luchang Wang et al., Analysis of measurement parameters related to Non-vascular intervention CT simulated lumbar percutaneous vertebroplasty, Journal of Interventional Radiology, Aug. 30, 2011, pp. 625-627, vol. 20, No. 8.

Jianzhe Li et al., Percutaneous perforation vertebroplasty in the treatment of osteoporotic vertebral compression fractures 102 cases, Chinese Journal of Gerontology, Jul. 10, 2013, pp. 3235-3236, vol. 33, No. 13.

* cited by examiner

INTELLIGENT PLANNING METHOD, DEVICE, EQUIPMENT AND MEDIUM FOR PUNCTURE PATH IN PVP SURGERY

CROSS REFERENCE TO RELATED APPLICATIONS

The present application claims the benefit of Chinese Patent Application No. 202310705522.0 filed on Jun. 15, 2023, the contents of which are incorporated herein by reference in their entirety.

TECHNICAL FIELD

The disclosure relates to the technical field of medical image processing, in particular to a method, device, equipment and medium for intelligent planning of puncture paths in PVP surgery.

BACKGROUND

The full name of PVP surgery is percutaneous vertebroplasty, which is a commonly used method to treat spinal compression fractures. This method mainly uses percutaneous puncture and specific instruments to inject bone cement into the diseased vertebral body to increase the strength and stability of the vertebral body. If the bone cement is injected well, the patient's compression fracture occurs in a short time, the patient may even be able to restore the previous height of the vertebral body. During the operation, it is necessary to ensure that the needle position is correct to avoid penetrating the inner wall of the vertebral pedicle and increasing the risk of nerve damage. In addition to the risk of nerve damage, if the injection technique is poor, bone cement extravasation may occur, which may cause pulmonary embolism or other complications. Therefore, accurate guidance and planning of the pedicle puncture path has become the most important thing before PVP surgery. At present, manual puncture path judgment is realized through intraoperative X-ray fluoroscopy. Preoperative planning of manual pedicle puncture path relies on doctor's experience. However, this method is highly subjective and lacks objectivity.

If computer-aided guidance planning is used, it is difficult to obtain relevant clinical data on bone cement leakage, so it is impossible to establish a judgment model about bone cement leakage in a short time, and furthermore, it is impossible to establish constraint strategies for the bone cement injection stop-point (i.e., the tip of the puncture needle) through the leakage judgment model. As artificial intelligence algorithms are increasingly used for intelligent processing of medical spatial images, the prediction of spatial key point positions has been well solved. For example, Chinese patent document CN115568943A discloses a path planning method for laminectomy surgery, which uses the SPU-Net network model to predict the positions of spatial key points in laminectomy surgery, and establishes the optimal surgical planning path based on the predicted position information of spatial key points. The pedicle puncture path can also achieve accurate key point prediction and guidance planning with the assistance of artificial intelligence algorithms. However, pedicle puncture and laminectomy decompression surgery are completely different surgical objects and surgical methods. The constraints and planning goals of the spatial path planning of the two are also completely different. A person skilled in the art cannot directly copy the methods in the above patent documents. In addition, Chinese patent document CN107157579A discloses a spinal pedicle screw implantation path planning method. This method discloses how to combine the preoperative planned puncture path and intraoperative imaging to obtain the entry point of actual intraoperative pedicle implantation. However, the preoperative planned puncture path in this patent document is completely determined based on traditional experience, that is, the key point is located at a position of the center point and end point of the vertebral pedicle at ⅓ of the middle and anterior of the vertebral body, which is the traditional way of spinal screw implantation. However, the above-mentioned empirical puncture path for spinal screw implantation is not suitable for percutaneous puncture of the vertebral body in PVP surgery, and it is difficult to ensure that bone cement does not leak. Therefore, how to guide the planning of the pedicle puncture path in PVP surgery to prevent bone cement leakage to the greatest extent has become an urgent technical problem that needs to be solved.

In addition, the acquisition of spinal vertebral body images during surgery is often achieved through a C-arm machine. The C-arm machine, the full name of C-arm X-ray machine, is a movable X-ray machine that integrates light, machine and image processing technology. It is one of the most commonly used surgical auxiliary tools in orthopedic surgery. When shooting, the image intensifier and tube of the C-arm machine are placed on both sides of the target area, the appropriate angle is adjusted, and a picture is taken to obtain the image. The clarity and accuracy of the original spinal vertebral body images acquired by the C-arm machine determine the reliability of the puncture path intelligent planning method in PVP surgery. However, since the X-ray source and X-ray detector at the end of the C-arm machine need to be connected to the control center in the base through cables, one end of the cable is connected to the body, and the other end is installed in the C-arm and extends to the X-ray source and X-ray detector on the C-arm. In order to facilitate the movement of the C-arm, it is necessary to reserve a certain length of the cable outside the C-arm and outside the body to avoid cable effect on C-arm movement. In addition, since the X-ray source and X-ray detector are in motion during detection, it is easy for cables to invade the sterile operating area during the movement of the X-ray source and X-ray detector, causing interference to the detection and requiring medical staff timely adjustment, which will not only affect the detection, but even affect the accuracy of the original spinal vertebral body image in severe cases, thereby affecting the accuracy of the puncture path intelligent planning method in PVP surgery.

SUMMARY

In view of the above-mentioned defects or deficiencies in the prior art, the present disclosure provides a method, device, equipment and medium for intelligent planning of puncture paths in PVP surgery, which can realize accurate guide planning to pedicle puncture paths with the assistance of artificial intelligence algorithms, prevent bone cement leakage.

One aspect of the present disclosure provides an intelligent planning method for puncture paths in PVP surgery, including:

intercepting a local CT image of a complete spinal vertebral body from an original spine CT image;

identifying a midpoint of a narrowest part of left and right vertebral pedicles and two theoretical puncture injection stop-points of left and right of the spinal vertebral body, from the local CT image of the complete spinal vertebral body through a trained neural network model, the theoretical puncture injection stop-points are optimal puncture injection stop-points without considering a leakage of bone cement;

calculating a distance $D_1$ from any theoretical puncture injection stop-point in the local CT image of the complete vertebral body to a middle plane in a front-back direction of the vertebral body, a distance $D_2$ from one of the theoretical puncture injection stop-points to a middle plane in a left-right direction of the vertebral body, and a shortest distance $D_3$ from the one of the theoretical puncture injection stop-points to a surface of a cortical bone of the vertebral body, taking a minimum value of the distance $D_1$, the distance $D_2$, and the distance $D_3$ as a radius of a space sphere area with each theoretical puncture injection stop-point as a sphere center; determining a radius of another space sphere area with the other one of the theoretical puncture injection stop-points as a sphere center according to a way similar to aforementioned method;

using a line connecting a midpoint of a narrowest part of any vertebral pedicle and any point in the space sphere area with a theoretical puncture injection stop-point as a sphere center, as an optional puncture path for the spinal vertebral body; wherein the theoretical puncture injection stop-point and the midpoint are at the same side.

Further, the method includes:

sampling coordinate points in the space sphere area with any theoretical puncture injection stop-point as the sphere center according to a preset sampling step, to obtain multiple candidate puncture injection stop-points;

calculating a value of a comprehensive distance D corresponding to each candidate puncture injection stop-points:

$$D = \frac{D_1 + D_4 + D_5}{D_6}$$

wherein $D_1$ represents the distance from any theoretical puncture injection stop-point to the middle plane in the front-back direction of the vertebral body, $D_4$ represents a minimum distance between a candidate puncture injection stop-point and a fracture surface, and $D_5$ represents a minimum distance between the candidate puncture injection stop-point and a fracture line, $D_6$ represents a minimum distance between the candidate puncture injection stop-point and the theoretical puncture injection stop-point;

using a candidate puncture injection stop-point with a largest comprehensive distance D is used as the optimal puncture injection stop-point in response to the leakage of bone cement being considered, and using a line connecting the midpoint of the narrowest part of the vertebral pedicle to the optimal puncture injection stop-point as the optimal puncture path in response to the leakage of bone cement being considered.

Further, the method includes:

marking the midpoints of the narrowest points of the left and right vertebral pedicles and the two theoretical puncture injection stop-points of left and right of the spinal vertebral body, in samples of the local CT image of multiple complete spinal vertebral body;

training a neural network model by using the marked samples of the local CT image to obtain the trained neural network model.

Further, the neural network model is an SPU-Net network model.

In another aspect, some embodiments of the present disclosure further provide an intelligent planning device for puncture path in PVP surgery, including:

an image interception module configured to intercept a local CT image of a complete spinal vertebral body from an original spine CT image;

an identification module configured to identify a midpoint of a narrowest part of left and right vertebral pedicles and two theoretical puncture injection stop-points of left and right, from the local CT image of the complete spinal vertebral body through a trained neural network model, the theoretical puncture injection stop-points are optimal puncture injection stop-points without considering a leakage of bone cement;

an injection-stop-point preliminary estimation module configured to calculate a distance $D_1$ from any theoretical puncture injection stop-point in the local CT image of the complete vertebral body to a middle plane in a front-back direction of the vertebral body, a distance $D_2$ from one of the theoretical puncture injection stop-points to a middle plane in a left-right direction of the vertebral body, and a shortest distance $D_3$ from the one of the theoretical puncture injection stop-points to a surface of a cortical bone of the vertebral body, take a minimum value of the distance $D_1$, the distance $D_2$, and the distance $D_3$ as a radius of a space sphere area with each theoretical puncture injection stop-point as a sphere center; determine a radius of another space sphere area with the other one of the theoretical puncture injection stop-points as a sphere center according to a way similar to aforementioned method;

a puncture path determination module configured to use a line connecting a midpoint of a narrowest part of any vertebral pedicle and any point in the space sphere area with a theoretical puncture injection stop-point as a sphere center, as an optional puncture path for the spinal vertebral body; wherein the theoretical puncture injection stop-point and the midpoint are at the same side.

Further, the device includes a sampling module configured to sample coordinate points in the space sphere area with any theoretical puncture injection stop-point as the sphere center according to a preset sampling step, to obtain multiple candidate puncture injection stop-points;

a comprehensive distance calculation module configured to calculate a value of a comprehensive distance D corresponding to each candidate puncture injection stop-points:

$$D = \frac{D_1 + D_4 + D_5}{D_6}$$

wherein $D_1$ represents the distance from any theoretical puncture injection stop-point to the middle plane in the front-back direction of the vertebral body, $D_4$ represents a minimum distance between a candidate puncture injection stop-point and a fracture surface, and $D_5$ represents a minimum distance between the candidate puncture injection stop-point and a fracture line, $D_6$ represents a minimum distance between the candidate puncture injection stop-point and the theoretical puncture injection stop-point;

an optimal-puncture-path determination module configured to use a candidate puncture injection stop-point with a largest comprehensive distance D is used as the optimal puncture injection stop-point in response to the leakage of bone cement being considered, and using a line connecting the midpoint of the narrowest part of the vertebral pedicle to the optimal puncture injection stop-point as the optimal puncture path in response to the leakage of bone cement being considered.

Further, the device includes: a training module configured to mark the midpoints of the narrowest points of the left and right vertebral pedicles and the two theoretical puncture injection stop-points of left and right of the spinal vertebral body, in samples of the local CT image of multiple complete spinal vertebral body, and train a neural network model by using the marked samples of the local CT image to obtain the trained neural network model.

Further, the neural network model is an SPU-Net network model.

In another aspect, some embodiments of the present disclosure further provide an electronic device, including: one or more processors; a memory configured to store one or more programs; when the one or more programs are executed by the one or more processors, the one or more processors are caused to implement the intelligent planning method for puncture path in PVP surgery as described above.

In another aspect, some embodiments of the present disclosure further provide a computer-readable storage medium, on which a computer program is stored, wherein when the computer program is executed by a processor, the intelligent planning method for puncture paths in PVP surgery as described above.

The puncture path planning and guidance method, device, equipment and medium provided by the present invention have the following beneficial effects.

The hard constraints of pedicle puncture are established through clinical experience. Under the hard constraints, the artificial intelligence algorithms are used to achieve the ideal position of the midpoint of the narrowest point of left and right vertebral pedicles and left and right injection stop-points of the spinal vertebral body. Accurate identification, and establish optional pedicle puncture paths based on the key points intelligently identified.

(2) Through statistical and correlation analysis of clinical data, the flexible constraints of the injection stop-point are obtained. Through the relationship between bone cement leakage and the minimum distance between the injection stop-point and the fracture surface and fracture line, the optimal puncture path is calculated from the above optional pedicle puncture path.

In another aspect, the present disclosure further provides a c-arm machine used for the intelligent planning method of the puncture path in the above-mentioned PVP surgery. The c-arm machine is configured to capture original spinal X-ray images during the operation. The c-arm machine includes a body, a movement unit, a c-shaped arm and a wire harness unit, an X-ray source, an X-ray detector and cables. The movement unit includes a lifting device, a first rotating device and a second rotating device connected in sequence, the lifting device Installed on the body, the c-shaped arm is installed on the second rotating device; the lifting device is configured to drive the first rotating device, the second rotating device and the c-shaped arm to lift; the first The rotating device is configured to drive the second rotating device and the c-shaped arm to rotate around the first horizontal axis, and the second rotating device is configured to drive the c-shaped arm to rotate around the second horizontal axis. The first horizontal axis and the second horizontal axis are perpendicular to each other. One end of the cable is connected to the body, and the other end extends into the c-shaped arm and is connected to the X-ray source and the X-ray detector; the wire harness unit is installed on the second rotating device and is configured to fix the cable to prevent the cable from intruding into the sterile operating area of the c-shaped arm when the movement unit drives the c-shaped arm to move.

Further, the wire harness unit includes a connection fixture, a first wire harness device and a second wire harness device installed on the connection fixture; the connection fixture includes a first mounting plate, a first connection mechanism and a second connection mechanism; the first connecting mechanism and the second connecting mechanism are respectively slidably installed at the opposite ends of the first mounting plate, and the two can be relatively close or far away; the first connecting mechanism includes oppositely arranged mounting base, a first locking bolt, a first clamping arm, a pressing assembly and a second clamping arm; the mounting base is provided on the first mounting plate, the mounting base is provided with a screw hole, and the first locking bolt is installed in the screw hole of the mounting base; the first clamping arm is connected to an end of the first locking bolt away from its own nut, and the first locking bolt can rotate axially so that the rotation of the first locking bolt in the screw hole can drive the first clamping arm to move; the pressing assembly is installed on a side away from the mounting base, of the first clamping arm. The second clamping arm is arranged opposite to the first clamping arm, and the pressing assembly and the second clamping arm can jointly clamp the second rotation device.

Further, the pressing assembly includes a first slider, a second slider, a first connecting rod, a second connecting rod, a third connecting rod, a fourth connecting rod, a first pressing block and a second pressing block; a first slide groove and a second slide groove are provided on the side away from the mounting base, of the first clamping arm, the first slider is slidably installed in the first slide groove, and the second slider is slidably installed in the second slide groove. The sides of the first pressing block and the second pressing block facing the second clamping arm have an arc surface; one end of the first connecting rod is hingedly connected to the first slider, the other end is hinged to the first pressing block; one end of the second connecting rod is hinged to the second slider, and the other end is hinged to the first pressing block; one end of the third connecting rod is hinged to the second slider, and the other end is hinged to the first clamping arm.

Further, the first wire harness device includes a first wire harness seat, a second wire harness seat, a second locking bolt and a pressing member; the first wire harness seat is installed on the first mounting plate, the first wire harness seat is provided with a first arc-shaped groove; one end of the second wire harness seat is hinged to one end of the first wire harness seat, and the other end is snap-fitted with the first wire harness seat; a second arc-shaped groove is provided on the side facing the first wire harness seat, of the second wire harness seat, and a screw hole is provided in the middle of the second wire harness seat; the second locking bolt is installed in the screw hole of the second wire harness the seat, and is located in the second arc-shaped groove; one end in the second arc-shaped groove, of the second locking bolt is installed with the pressing member.

Further, the second wire harness device includes a sliding plate, an elastic member, a first wire harness pulley, a second wire harness pulley, a third wire harness pulley, a first rotating shaft, a first damping rotating shaft and a second damping rotating shaft; a third slide groove is provided on the first mounting plate, and the sliding plate is slidably installed in the third slide groove in a direction that can approach or move away from the first wire harness device; the elastic member is are respectively connected to the third slide groove and the sliding plate; the first wire harness pulley is rotatably installed on the sliding plate through a first rotating shaft, and the second wire harness pulley is installed on the sliding plate through the first damping rotating shaft, the third wire harness pulley is installed on the sliding plate through the second damping rotating shaft. The distance between the second wire harness pulley and the third wire harness pulley is adjustable.

For the technical problems solved and the technical effects brought by the above technical solutions, please refer to the corresponding descriptions in the specific embodiments section and will not be described again here.

BRIEF DESCRIPTION OF FIGURES

Other features, objects and advantages of the present disclosure will become more apparent by reading the detailed description of the non-limiting embodiments with reference to the following drawings.

DETAILED DESCRIPTION

Figure 1:
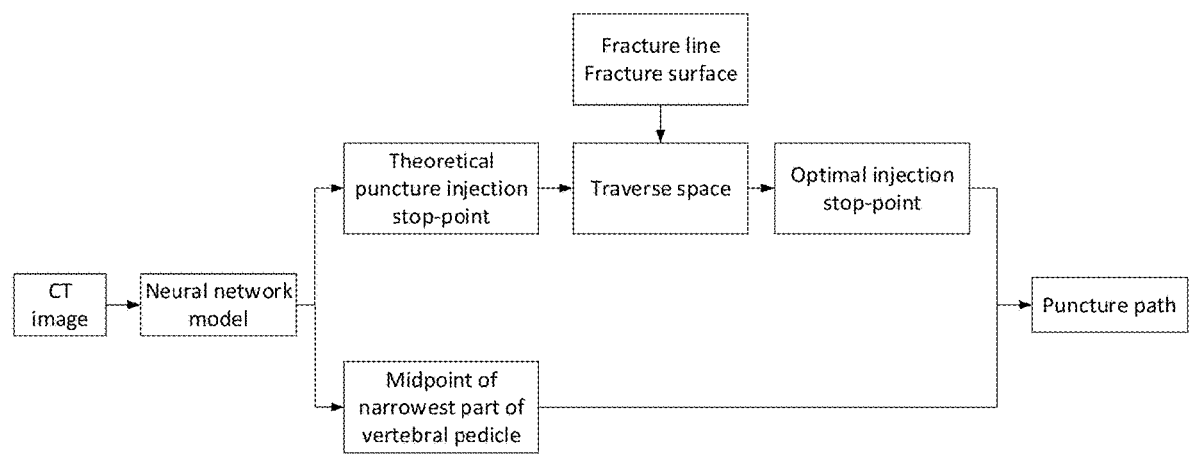
FIG. 1 is a schematic diagram of the spinal vertebral pedicle puncture path planning provided by an embodiment of the present disclosure.

In order to make the purpose, technical solutions and advantages of the embodiments of the present disclosure clearer, the technical solutions in the embodiments of the present disclosure will be clearly and completely described below in conjunction with the drawings in the embodiments of the present disclosure. Obviously, the described embodiments are a part of embodiments of the present disclosure, but not all embodiments. Based on the embodiments of the present disclosure, all other embodiments obtained by those of ordinary skill in the art without making creative efforts fall within the scope of protection of the present disclosure.

Terms used in the embodiments of the present disclosure are only for the purpose of describing specific embodiments, and are not intended to limit the present disclosure. As used in this embodiment and the appended claims, the singular form "a kind of" is intended to include the plural forms as well, unless the context clearly dictates otherwise.

It should be understood that although terms such as first, second, and third may be used to describe the acquisition modules in the embodiments of the present disclosure, these acquisition modules should not be limited to these terms. These terms are only used to distinguish acquisition modules from one another.

Depending on the context, the word "if" as used herein may be interpreted as "when" or "while" or "in response to determination" or "in response to detection." Similarly, depending on the context, the phrases "if determined" or "if detected (the stated condition or event)" could be interpreted as "when determined" or "in response to the determination" or "when detected (the stated condition or event)" or "in response to detecting (a stated condition or event)".

It should be noted that the directional terms such as "upper", "lower", "left" and "right" described in the embodiments of the present disclosure are described from the perspective shown in the drawings and should not be understood as limiting the implementation of the present disclosure. Also in this context, it also needs to be understood that when it is mentioned that an element is formed "on" or "under" another element, it can not only be directly formed "on" or "under" another element, but also can be formed "on" or "under" another element. An element is indirectly formed "on" or "below" another element through intervening elements.

EXAMPLES

The full name of PVP surgery is Percutaneous Vertebroplasty (PVP), which is a commonly used method to treat spinal compression fractures. This method mainly uses percutaneous puncture and specific instruments to inject bone cement into the vertebral body to increase the strength and stability of the vertebral body. Injecting bone cement can not only enhance the stability and strength of the vertebral body, but also prevent the vertebral body from continuing to collapse and relieve pain, thereby mitigating the progression of osteoporosis. If the bone cement is injected well, the patient's compression fracture occurs in a short time, the patient may even be able to restore the previous height of the vertebral body. This treatment method is easy to understand. It is like having a pillar at home. When cracks appear due to wind and sun, cement or steel bars need to be used to strengthen the pillar. The difference is that cement can be placed on the outside to strengthen the pillars, while bone cement must be injected into the inside to strengthen the vertebral body.

In order to avoid bone cement extravasation, it is necessary to plan a reasonable puncture path for the spinal vertebral body, that is, designing a reasonable puncture start point and stop point, and performing the puncture operation of the puncture needle according to the planned path. In order to obtain a reasonable puncture path, the present disclosure comprehensively considers clinical experience, clinical data, bone cement leakage conditions, and constraint conditions, and finally obtains an intelligent planning method for puncture path in PVP surgery.

FIG. 1 is a schematic diagram of algorithmic logic of the intelligent planning method for puncture path in PVP surgery provided by an embodiment of the present disclosure.

Figure 2:
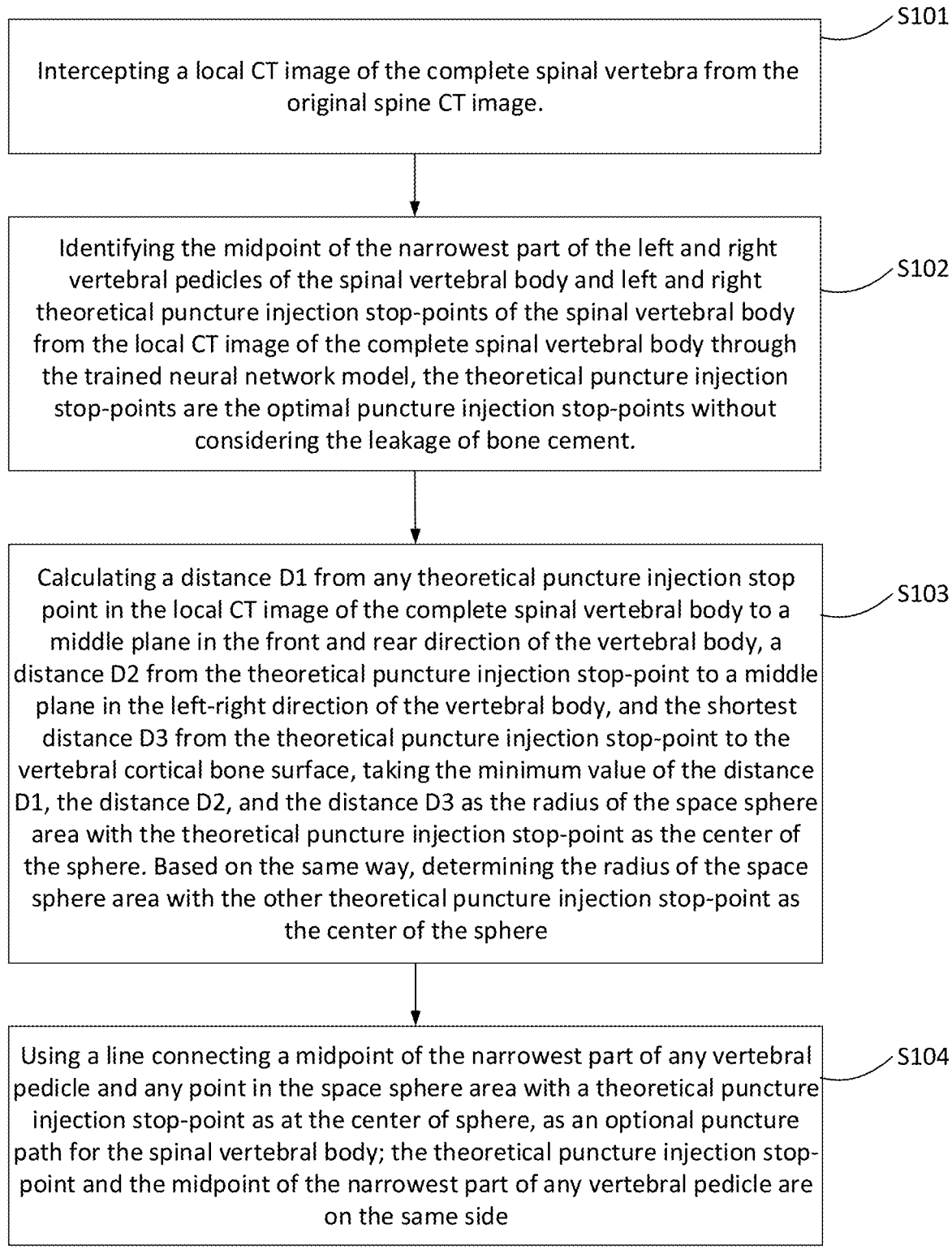
FIG. 2 is a flow chart of obtaining an optional puncture path by an intelligent planning method for a puncture path in a PVP operation provided by an embodiment of the present disclosure.

As shown in FIG. 2, the intelligent planning method for puncture path in PVP surgery of the present disclosure includes the following steps:

Step S101, intercepting a local CT image of the complete spinal vertebra from the original spine CT image.

Specifically, in this embodiment, it is preferable that the spine image is a CT image of the spine. The local CT image of the original spine CT image is intercepted by the image recognition and segmentation algorithm, and a local CT image containing only one complete spinal vertebral body is obtained. The above-mentioned image recognition and segmentation algorithm is a relatively common algorithm in the field, which belongs to the prior art, and will not be described in detail in this embodiment.

Step S102, identifying the midpoint of the narrowest part of the left and right vertebral pedicles of the spinal vertebral body and left and right theoretical puncture injection stop-points of the spinal vertebral body from the local CT image of the complete spinal vertebral body through the trained neural network model, the theoretical puncture injection stop-points are the optimal puncture injection stop-points without considering the leakage of bone cement.

Specifically, based on statistical analysis of clinical surgical cases, the inventor found that the puncture is safest when the injection start-point of the puncture needle is the midpoint of the narrowest parts of the left and right vertebral pedicles of the spinal vertebral body. When the injection stop-point of the puncture needle is not located outside the vertebral body, the two injection stop-points are distributed on the left and right parts of the vertebral body, and located in the front half of the vertebral body, the puncture trajectory formed by the injection start-point and the injection stop-point can only guarantee the treatment effect of the bone cement injected by the puncture needle be the best, and the puncture is the safest.

In order to identify the injection start-point and injection stop-point that meet the above conditions, the present disclosure uses a pre-trained neural network model to predict local contrastographic images with complete spinal vertebral body. Preferably, the neural network model can adopt the SPU-Net spatial key point detection model mentioned in the Chinese patent document CN115568943A. The neural network of the SPU (Spatialpyramid upsampling) structure can realize the unification of the size of the multi-scale feature image to realize the feature fusion of the feature image. The SPU-Net first uses a CBR module to compress and unify the number of feature channels of each feature map to reduce the amount of subsequent calculations. After realizing the compression and unification of the number of feature channels of each feature image, the SPU-Net uses 3D Patch Expanding to achieve shape unification. The SPU-Net stitches each feature image of uniform size in the feature dimension, and inputs it into OutLayer (3D Conv+3D BatchNorm+Softmax) for processing, and obtains a thermal image of the quantity same as the quantity of key points in the target space. Finally, the precise positioning of the corresponding spatial key points can be achieved only by finding the point with the highest brightness in each channel.

When training the neural network model, marking the midpoint of the narrowest part of the left and right vertebral pedicles and the two (left and right) theoretical puncture injection stop-points of the spinal vertebral body in multiple local CT image samples of complete vertebral body. The marked local CT image samples are used for training the neural network model to obtain the trained neural network model. This embodiment does not go into details.

Step S103, calculating a distance $D_1$ from any theoretical puncture injection stop point in the local CT image of the complete spinal vertebral body to a middle plane in the front and rear direction of the vertebral body, a distance $D_2$ from the theoretical puncture injection stop-point to a middle plane in the left-right direction of the vertebral body, and the shortest distance $D_3$ from the theoretical puncture injection stop-point to the vertebral cortical bone surface, taking the minimum value of the distance $D_1$, the distance $D_2$, and the distance $D_3$ as the radius of the space sphere area with the theoretical puncture injection stop-point as the center of the sphere. Based on the same way, determining the radius of the space sphere area with the other theoretical puncture injection stop-point as the center of the sphere.

Figure 3:
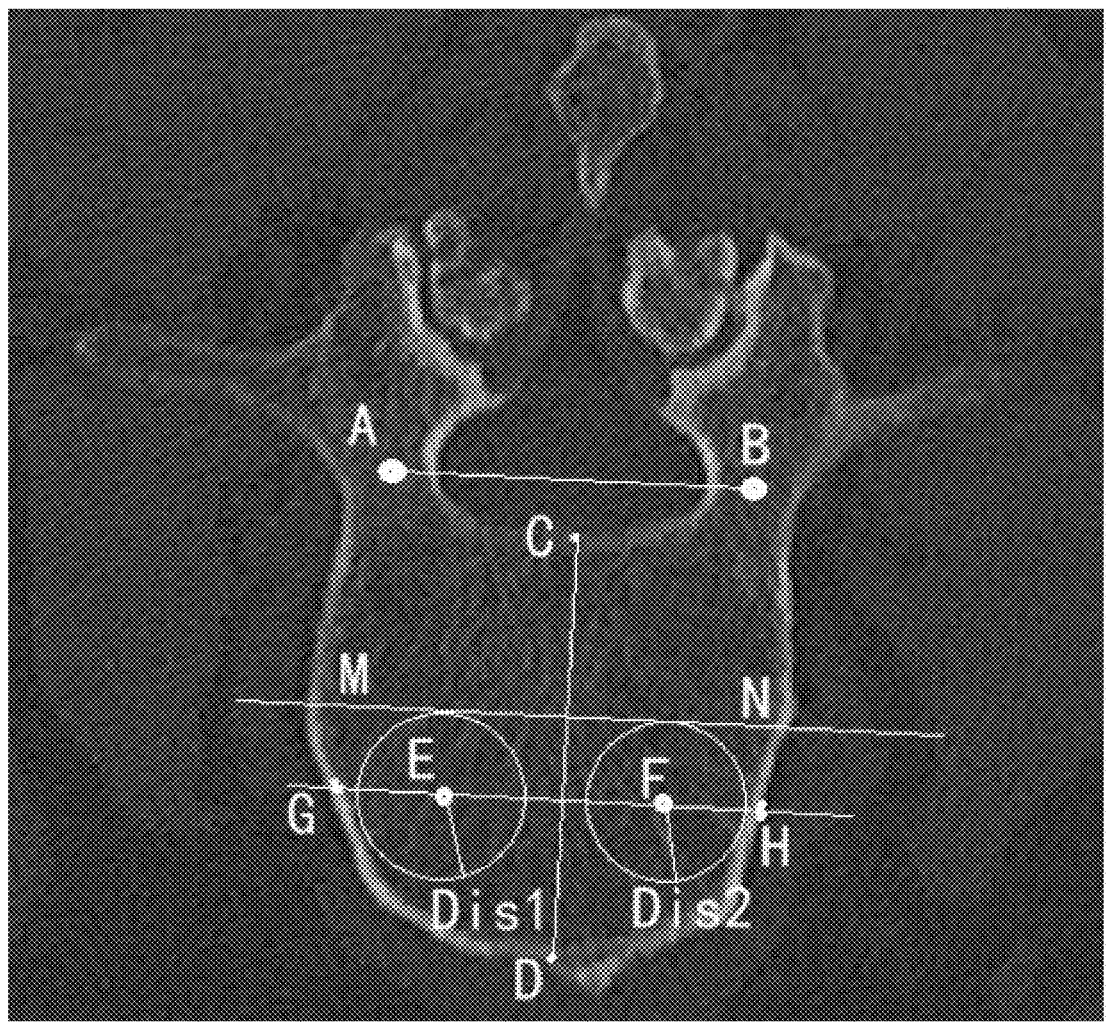
FIG. 3 is a schematic diagram of the geometric relationship between the start point and the injection stop-point of spinal vertebral body puncture provided by an embodiment of the present disclosure.

As shown in FIG. 3, after predicting the midpoints A and B of the narrowest parts of the left and right vertebral pedicles of the spinal vertebral body and the left and right theoretical puncture injection stop-points E and F of the vertebral body through the neural network model, since the prediction result of the neural network is only the theoretical puncture position, so it is necessary to calculate the possible coverage area of all candidate puncture injection stop-points based on hard constraints.

The specific hard constraints and calculation process are as follows:

calculating the distance $D_1$ from point E (left theoretical puncture injection stop-point) to the middle plane of the vertebral body in the front and rear direction (shown as the MN plane in FIG. 3, M and N are intersection points on the front and rear edge of the vertebral body, of a straight line obtained by the middle plane of the vertebral body in the front and rear direction intersecting with a section of the vertebral body shown in FIG. 3), and the distance $D_2$ from point E to a middle plane of the vertebral body in the left-right direction (shown as CD plane in FIG. 3, C and D are intersection points on the front and rear edge of the vertebral body, of a straight line obtained by the middle plane of the vertebral body in the left-right direction intersecting with a section of the vertebral body shown in FIG. 3), and the shortest distance $D_3$ from the vertebral cortical bone surface (indicated by point G), then taking the smaller value among values of $D_1$-$D_3$ as the radius Dis1 of a space sphere area; traversing the space area forms a spherical area with point E as the center and Dis1 as the radius. All candidate puncture injection stop-points on the left are located in this space sphere area.

Based on the same method, calculating the distance $D_1$ from point F (right theoretical puncture injection stop-point) to the middle plane in the front and rear direction of the vertebral body (shown as the MN plane in FIG. 3) and point F (right theoretical puncture injection stop-point), the distance $D_2$ to the middle plane in the left-right directions of the vertebral body (shown as the CD plane in FIG. 4), and the shortest distance $D_3$ from the vertebral cortical bone surface (point H), and then taking the smaller value among values of $D_1$-$D_3$ as the radius Dis2 of a space sphere area; traversing the space area forms a spherical area with point F as the center and Dis2 as the radius. All the candidate puncture injection stop-points on the right are located in this space sphere area.

Step S104, using a line connecting a midpoint of the narrowest part of any vertebral pedicle and any point in the space sphere area with a theoretical puncture injection stop-point as at the center of sphere, as an optional puncture path for the spinal vertebral body; the theoretical puncture injection stop-point and the midpoint of the narrowest part of any vertebral pedicle are on the same side.

Specifically, as shown in FIG. 3, the line connecting the midpoint A of the narrowest part of the left vertebral pedicle with any point in the space sphere area with the left theoretical puncture injection stop-point E as the center of sphere is taken as the optional puncture path of the left vertebral pedicle of the spinal vertebral body. In the same way, the line connecting the midpoint B of the narrowest part of the right vertebral pedicle and any point in the space sphere area with the right theoretical puncture stop-point F as the center of sphere is taken as the optional puncture path of the right vertebral pedicle of the spinal vertebral body.

Figure 4:
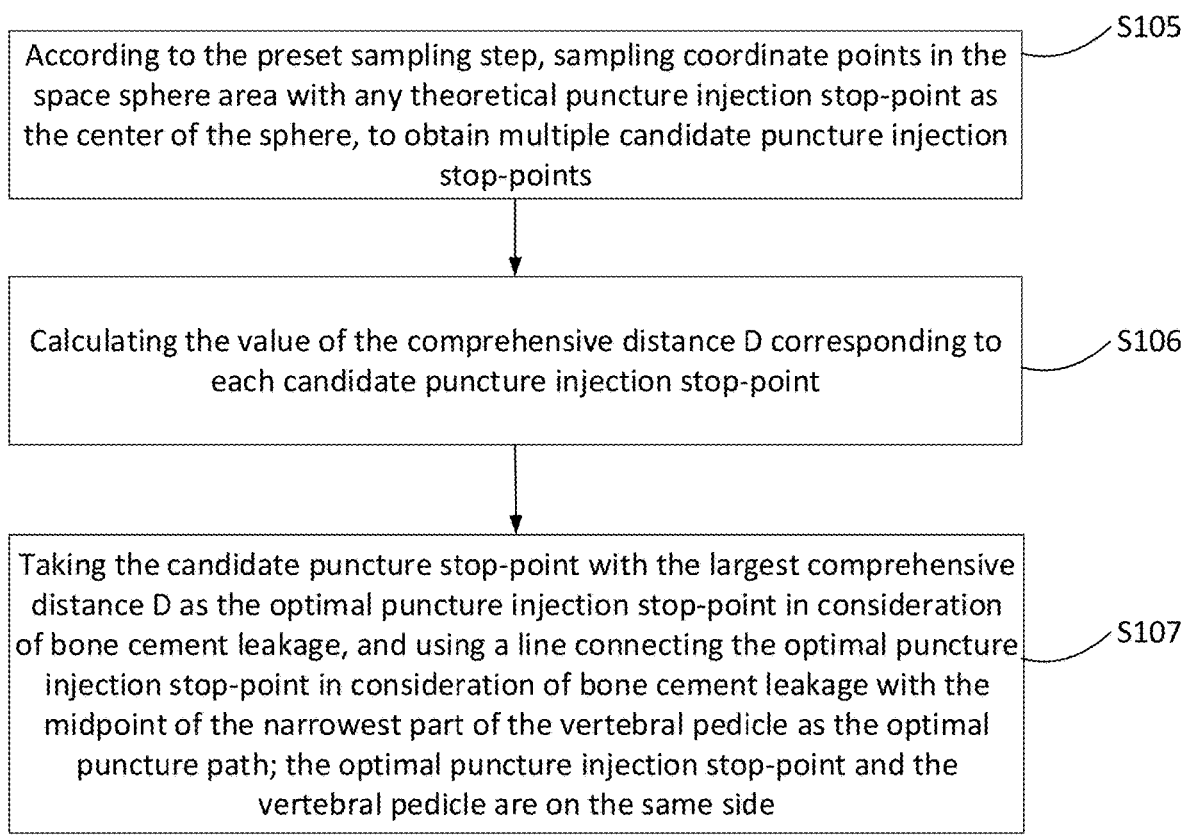
FIG. 4 is a flow chart of obtaining an optimal puncture path by an intelligent planning method for a puncture path in a PVP operation provided by an embodiment of the present disclosure.

The above steps S101 to S104 obtain the optional puncture path of the vertebral pedicle, that is, any puncture path can be used as the minimum allowable puncture path for subsequent PVP surgery. However, in PVP surgery, it is often desired to not only ensure the safety of the puncture path (without damaging blood vessels and nerves), but also to ensure that the injected bone cement has the lowest probability of leakage. In order to achieve the above technical effects, the present disclosure further provides a solution for further determining the optimal puncture path, as shown in FIG. 4, including the following steps:

Step S105, according to the preset sampling step, sampling coordinate points in the space sphere area with any theoretical puncture injection stop-point as the center of the sphere, to obtain multiple candidate puncture injection stop-points.

Specifically, the step S104 obtains a space sphere area with the theoretical puncture injection stop-point as the center of the sphere. This space sphere area is a space area under hard constraints. In theory, there are countless candidate puncture injection stop-points. In order to obtain the optimal injection stop-point, the sampling step is set in this step, and according to the preset sampling step, coordinate points in the space sphere area with the theoretical puncture injection stop-point as the center of the sphere are sampled to ensure that finite candidate puncture injection stop-points are obtained.

Step S106, calculating the value of the comprehensive distance D corresponding to each candidate puncture injection stop-point:

$$D = \frac{D_1 + D_4 + D_5}{D_6}.$$

$D_1$ represents the distance from the theoretical puncture injection stop-point to the middle plane in the front-back direction of the vertebral body. $D_4$ represents the minimum distance between the candidate puncture injection stop-points and the fracture surface, and $D_5$ represents the minimum distance between the candidate puncture injection stop-points and the fracture line. $D_6$ represents the minimum distance between the candidate puncture injection stop-points and the theoretical puncture injection stop-point.

This step is based on the relationship between the minimum distance between the candidate puncture injection stop-points and the fracture surface, and the minimum distance between the fracture surface and the minimum distance between the candidate puncture injection stop-points and the fracture line, the distance between the candidate puncture injection stop-points and the middle plane in the front and rear direction of the vertebral body (see the MN plane in FIG. 3), the distance between the candidate puncture injection stop-points and the theoretical puncture injection stop-point, to select the optimal puncture injection stop-point. Specifically, the farther the injection stop-points are from the fracture line and fracture surface, the smaller the chance of bone cement leakage is. The candidate puncture injection stop-point should be as far away as possible from the middle plane in the front and rear direction of the vertebral body, so that leakage of bone cement to the back of the vertebral body, that is, into the spinal canal, can be avoided as much as possible. The theoretical puncture injection stop-point is the optimal position without considering bone cement leakage, so the candidate puncture injection stop-points should be closer to the theoretical puncture injection stop-points. Therefore, an evaluation index called comprehensive distance D is set in this step, which is used to evaluate the comprehensive distance between the candidate puncture injection stop-points and the fracture line, the fracture surface, the middle plane in the front and rear of the vertebral body, and the theoretical puncture injection stop-point. The above formula and parameters can be referred for more details.

Step S107, taking the candidate puncture stop-point with the largest comprehensive distance D as the optimal puncture injection stop-point in consideration of bone cement leakage, and using a line connecting the optimal puncture injection stop-point in consideration of bone cement leakage with the midpoint of the narrowest part of the vertebral pedicle as the optimal puncture path; the optimal puncture injection stop-point and the vertebral pedicle are on the same side.

Figure 5:
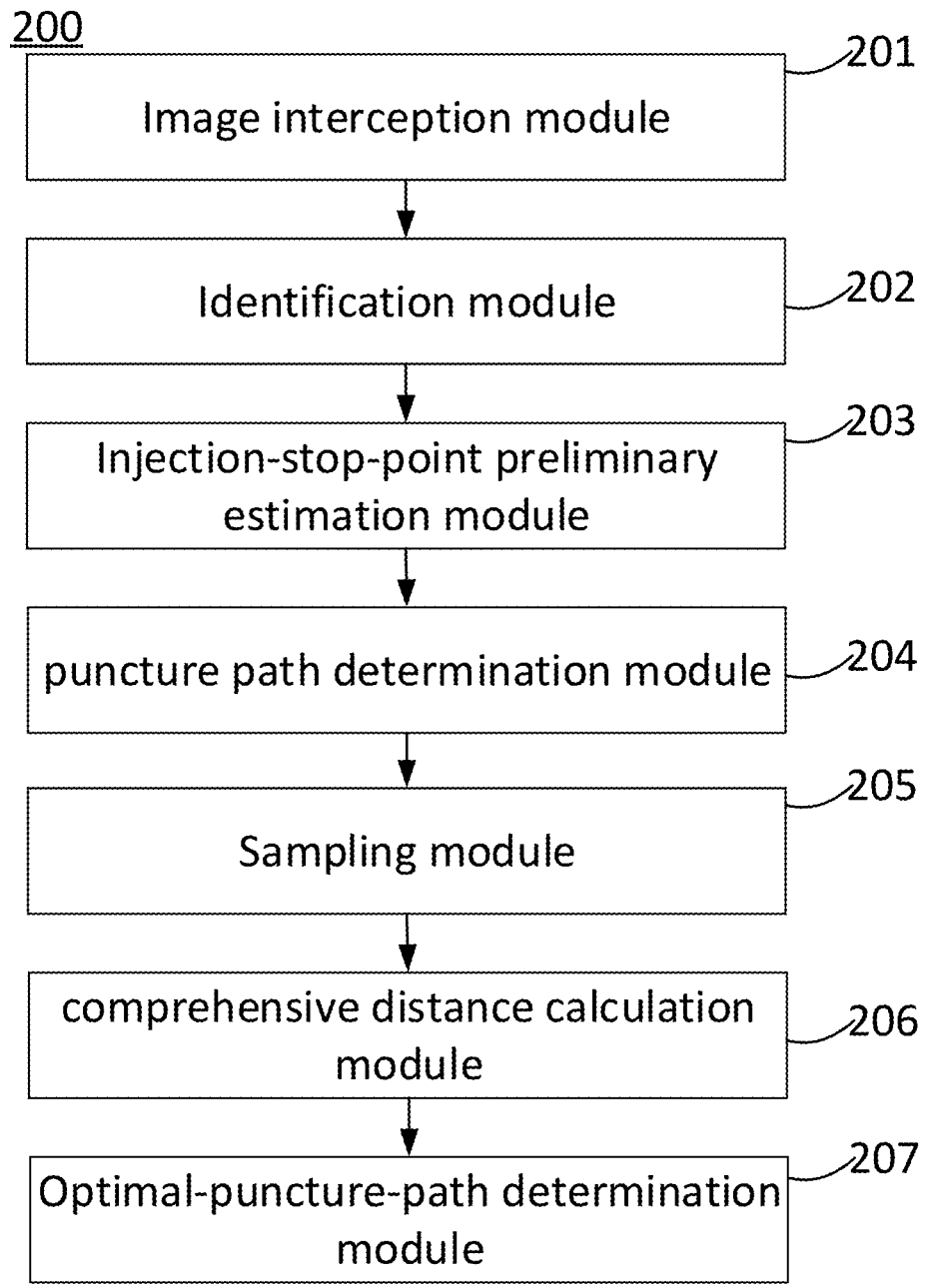
FIG. 5 is a schematic structural diagram of an intelligent planning device for puncture paths in PVP surgery provided by another embodiment of the present disclosure.

As shown in FIG. 5, another embodiment of the present disclosure further provides an intelligent puncture path planning device 200 in PVP surgery, including an image interception module 201, an identification module 202, an injection-stop-point preliminary estimation module 203, and a puncture-path-determination module 204. The puncture path planning device 200 can be used to perform various steps in the above method embodiment.

Specifically, the intelligent puncture path planning device 200 in PVP surgery includes:

the image interception module 201 configured to intercept a local CT image of the complete spinal vertebral body from the original spine CT images;

the identification module 202 configured to identify a midpoint of the narrowest parts of the left and right vertebral pedicles of the spinal vertebral body and left and right theoretical puncture injection stop-points of the vertebral body from the local CT image of the complete spinal vertebral body through a trained neural network model. The theoretical puncture injection stop-points are the optimal puncture injection stop-points without considering bone cement leakage.

the injection-stop-point preliminary estimation module 203 configured to calculate the distance $D_1$ from any theoretical puncture injection stop-point in the local CT image of the complete spinal vertebral body to the middle plane in the front and rear direction of the vertebral body, and the distance $D_2$ from the theoretical puncture injection stop-point to the middle plane in the left-right direction of the vertebral body, and the shortest distance $D_3$ from the theoretical puncture stop-point to the surface of the vertebral cortical bone, take the minimum value of the distance $D_1$, the distance $D_2$, the and distance $D_3$ as the radius of the space sphere with the theoretical puncture injection stop-point as the center of the sphere; determine the radius a the space sphere area with another theoretical puncture injection stop-point as the center of the sphere based on the same method;

the puncture path determination module 204 configured to use a line connecting the midpoint of the narrowest part of any vertebral pedicle to any point in the space sphere area with the theoretical puncture injection stop-point as the center of the sphere, as the optional puncture path; the theoretical puncture injection stop-point and the midpoint are on the same side.

Furthermore, the intelligent puncture path planning device 200 in PVP surgery further includes:

a sampling module 205 configured to sample coordinate points in the space sphere area with any theoretical puncture injection stop-point as the center of the sphere according to a preset sampling step, to obtain multiple candidate puncture injection stop-points;

a comprehensive distance calculation module 206 configured to calculate a value of the comprehensive distance D corresponding to each candidate puncture injection stop-point:

$$D = \frac{D_1 + D_4 + D_5}{D_6}.$$

$D_1$ represents the distance from the theoretical puncture injection stop-point to the middle plane in the front-back direction of the vertebral body. $D_4$ represents the minimum distance between the candidate puncture injection stop-points and the fracture surface, and $D_5$ represents the minimum distance between the candidate puncture injection stop-points and the fracture line. $D_6$ represents the minimum distance between the candidate puncture injection stop-points and the theoretical puncture injection stop-point;

an optimal-puncture-path determination module 207 configured to use the candidate puncture injection stop-point with the largest comprehensive distance D as the optimal puncture injection stop-point considering bone cement leakage, and use a line connecting the optimal puncture injection stop-point and the midpoint of the narrowest part of the vertebral pedicle as the optimal puncture path; the optimal puncture injection stop-point and the midpoint are on the same side.

It should be noted that the vertebral body puncture path planning guidance device 200 provided in this embodiment corresponds to a technical solution that can be used to perform each method embodiment. Its implementation principles and technical effects are similar to those of the method, and will not be described again here.

Figure 6:
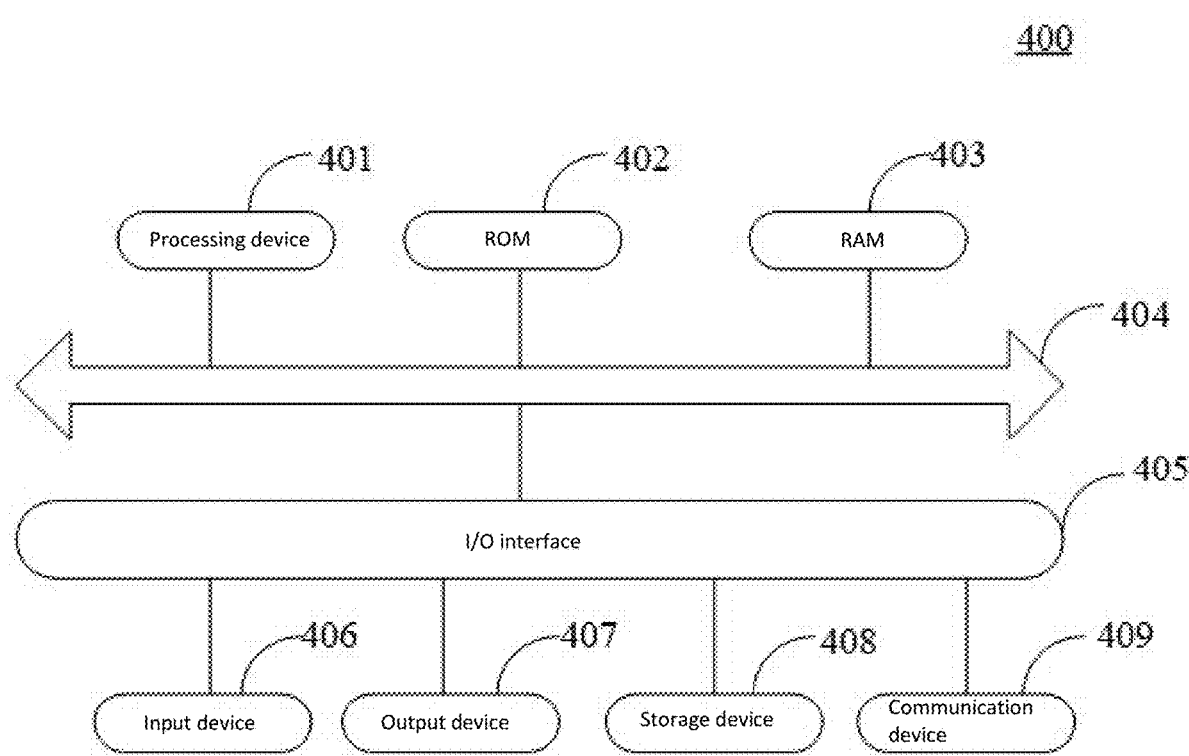
FIG. 6 is a schematic structural diagram of an electronic device provided by another embodiment of the present disclosure.
Figure 7:
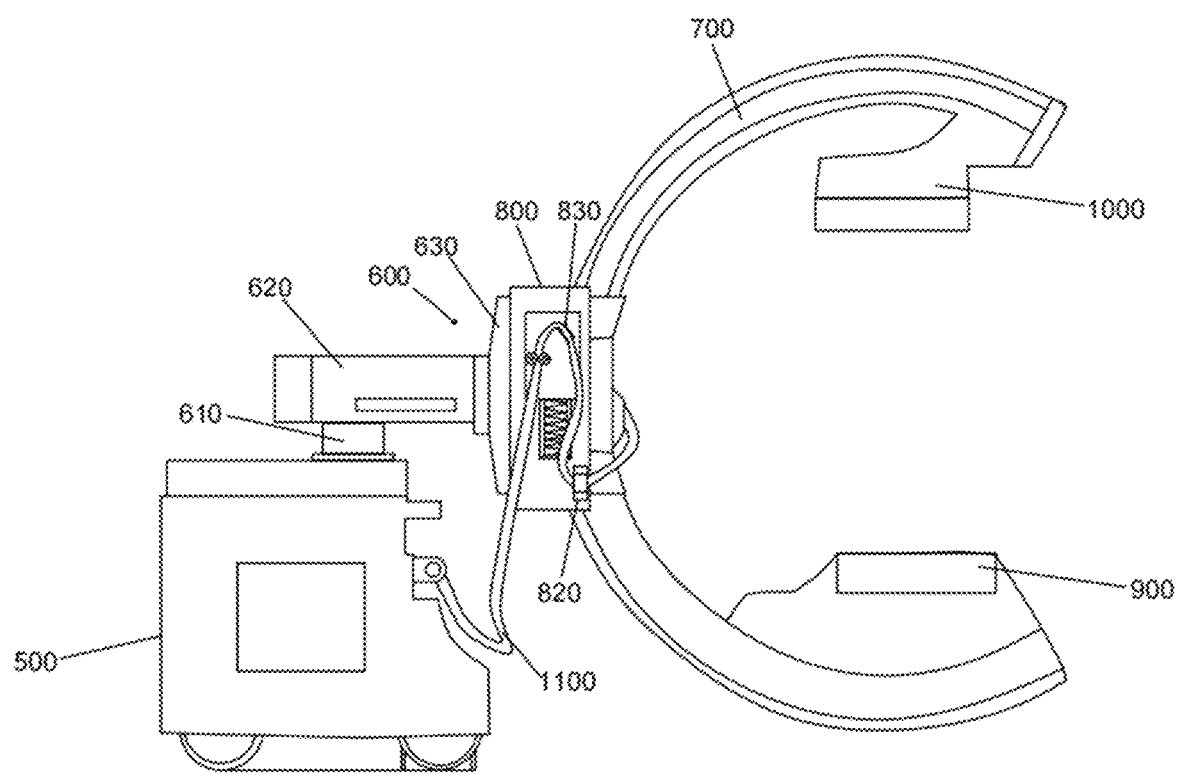
FIG. 7 is a schematic structural diagram of a C-arm machine provided by another embodiment of the present disclosure.

FIG. 6 is a schematic structural diagram of an electronic device according to another embodiment of the present disclosure. The electronic device 400 in the embodiment of the present disclosure may include, but is not limited to, terminal devices such as notebook computers, PADs (tablet computers), desktop computers, PVP surgical robots, and the like. The electronic device shown in FIG. 7 is only an example and should not impose any restrictions on the functions and scope of use of the embodiments of the present disclosure.

As shown in FIG. 6, the electronic device 400 may include a processing device 401 (e.g., central processing unit, graphics processor, etc.), which executes various appropriate actions and processes to implement the methods of the embodiments of the present disclosure according to a program stored in a Read-Only Memory (ROM) 402 or a program loaded into a Random Access Memory (RAM) from a storage device 408. In the RAM 403, various programs and data necessary for the operation of the electronic device 400 are also stored. The processing device 401, ROM 402 and RAM 403 are connected to each other through a bus 404. An input/output (I/O) interface 405 is also connected to the bus 404.

Generally, the following devices may be connected to the I/O interface 405: an input device 406 including, for example, a touch screen, a touch pad, a keyboard, mouse, a camera, a microphone, an accelerometer, a gyroscope, etc., an output device 407 including, for example, a liquid crystal display (LCD), a speaker, a vibrator, a storage device 408 including a magnetic tape, a hard disk, etc. and a communication device 409. The communication device 409 may allow the electronic device 400 to communicate wirelessly or wire with other devices to exchange data. Although FIG. 6 illustrates the electronic device 400 with various means, it should be understood that implementation or availability of all illustrated means is not required. More or fewer means may alternatively be implemented or provided.

In particular, according to an embodiment of the present disclosure, the processes described above with reference to the flow chart may be implemented as computer software programs. For example, embodiments of the present disclosure include a computer program product including a computer program carried on a non-transitory computer-readable medium. The computer program includes program codes for executing the method shown in the flow chart, thereby achieving the above the method described. In such embodiments, the computer program may be downloaded and installed from the network via communication device 409, or installed from storage device 408, or from ROM 402. When the computer program is executed by the processing device 401, the above functions defined in the method of the embodiment of the present disclosure are performed.

In another embodiment of the present disclosure, the clarity, accuracy, etc. of the original spinal image obtained by the C-arm machine determine the reliability of the intelligent puncture path planning method in the PVP surgery of the method embodiment. However, the applicant discovered during the process of obtaining original spinal contrastographic images through the C-arm machine, since the X-ray source and X-ray detector at the end of the C-arm machine need to be connected to the control center in the base through cables, of which one end is connected to the body of C-arm machine, and the other end is installed in the C-shaped arm and extends to the X-ray source and X-ray detector on the C-shaped arm. In order to facilitate the movement of the C-shaped arm, a certain length of portion of the cables outside the C-shaped arm and the body of C-arm machine need to be reserved to avoid the influence of cables on the movement of the C-arm.

Since the X-ray source and X-ray detector are in motion during detection, it is easy for cables to invade the sterile operating area during the movement of the X-ray source and X-ray detector, causing interference to the detection, and medical staffs are required to remove them in time, which will not only affect the detection, but in severe cases may even affect the accuracy of the original spinal contrastographic image, thereby affecting the accuracy of the intelligent puncture path planning method in PVP surgery.

In view of this, this embodiment provides a C-arm machine, which solves the above technical problems by adding a wire harness unit to the C-arm machine.

As shown in FIG. 7, the C-arm machine provided in this embodiment includes: a body 500, a movement unit 600, a C-shaped arm 700, a wire harness unit 800, an X-ray source 900, an X-ray detector 1000 and other functional structures.

In the above functional structure, the body 500 of this embodiment has the same or similar structure as the existing C-arm machine. Therefore, this embodiment does not describe the internal structure of the body 500 with drawings.

In the above functional structure, the movement unit 600 of this embodiment includes a lifting device 610, a first rotating device 620 and a second rotating device 630 connected in sequence. The lifting device 610 is installed on the body 500, and the C-shaped arm 700 is installed on the second rotating device 630 in this embodiment. The lifting device 610 in this embodiment is configured to drive the first rotating device 620, the second rotating device 630 and the C-shaped arm 700 to go up and down. The first rotating device 620 in this embodiment is configured to drive the second rotating device 630 and the C-shaped arm 700 to rotate around the first horizontal axis. The second rotating device 630 of this embodiment is configured to drive the C-shaped arm 700 to rotate around the second horizontal axis. The first horizontal axis and the second horizontal axis are perpendicular to each other.

One end of the cable 1100 is connected to the body 500, and the other end extends into the C-shaped arm 700 of this embodiment and is connected to the X-ray source 900 and the X-ray detector 1000 of this embodiment.

In the above functional structure, the wire harness unit 800 of this embodiment is installed on the second rotating device 630 of this embodiment, and is configured to perform fixed control of the cable 1100 to prevent the cable 1100 invading the sterile operating area of the C-shaped arm 700 when the C-shaped arm 700 is driven to move by the movement unit 600, and does not affect the original movement of the cable 1100 following the movement unit 600. In addition, the wire harness unit 800 of this embodiment can also be adapted to different models of C-arm machine produced by different manufacturers.

Figure 8:
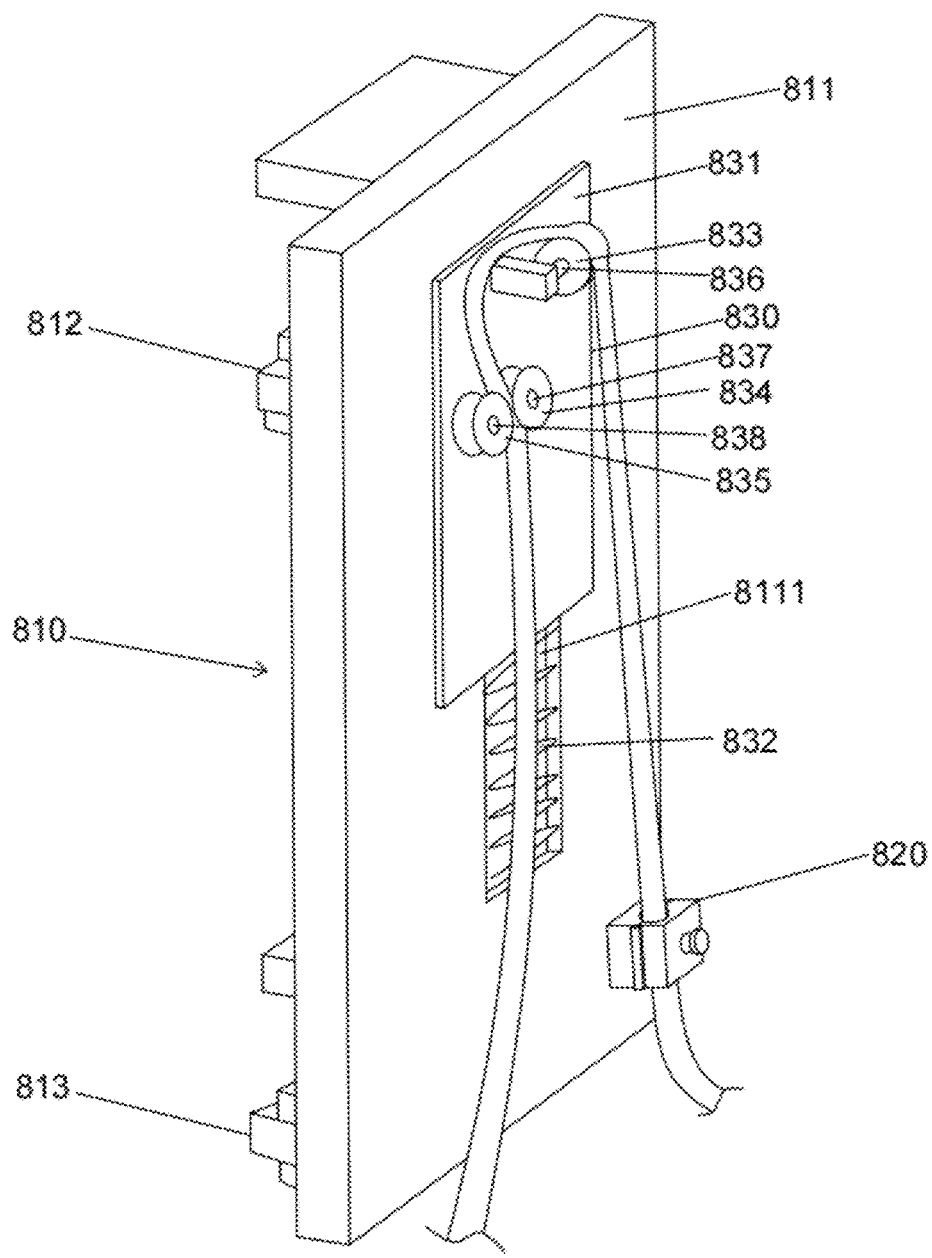
FIG. 8 is a schematic structural diagram of a wire harness unit of a C-arm machine provided by another embodiment of the present disclosure.

As shown in FIG. 8, the wire harness unit of this embodiment includes functional devices such as a connection fixture 810 and a first wire harness device 820 and a second wire harness device 830 installed on the connection fixture 810.

Among the above functional devices, the connection fixture 810 of this embodiment includes a first mounting plate 811, a first connection mechanism 812 and a second connection mechanism 813. The first connection mechanism 812 and the second connection mechanism 813 are respectively slidably installed on opposite ends of the first mounting plate 811 in this embodiment, and can be relatively close or far apart to adapt to the second rotating device 630 of different sizes. The specific sliding form is not limited and can be any kind of sliding connection.

Figure 10:
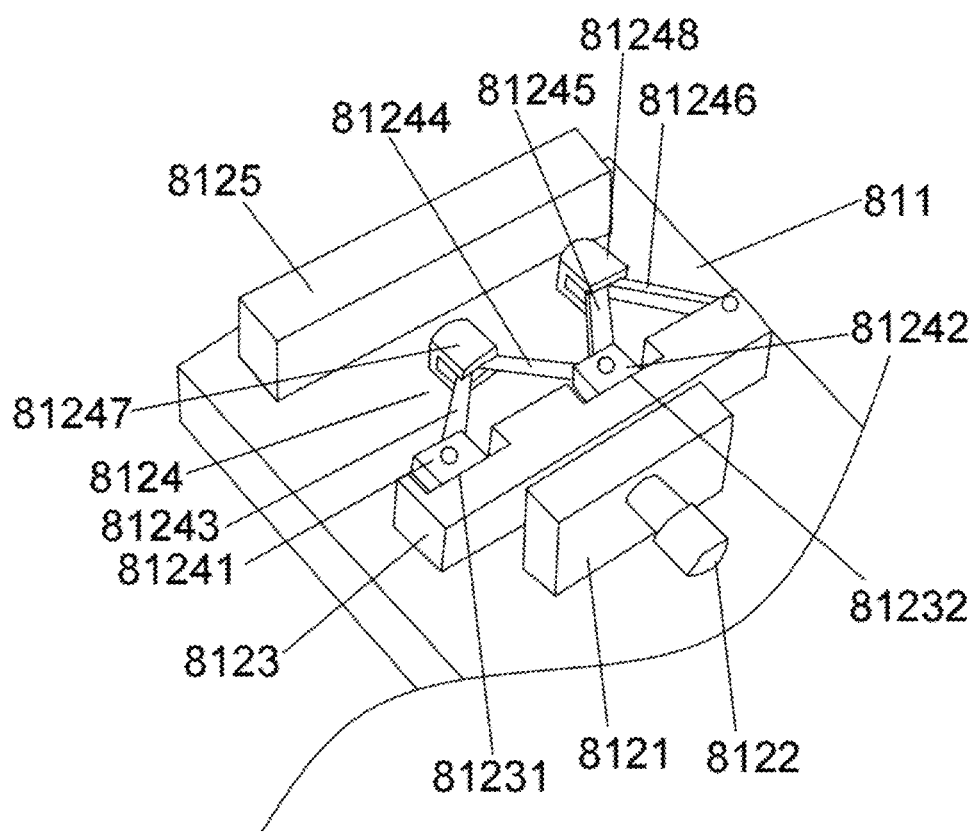
FIG. 10 is a schematic structural diagram of a first connection mechanism provided by another embodiment of the present disclosure.

As shown in FIG. 10, the first connection mechanism 812 of this embodiment includes an a mounting base 8121, a first locking bolt 8122, a first clamping arm 8123, a pressing assembly 8124 and a second clamp arm 8125 arranged relatively. The mounting base 8121 is provided on the first mounting plate 811 of this embodiment. The mounting base 8121 is provided with a screw hole. The first locking bolt 8122 is installed in the screw hole of this embodiment.

The first clamping arm 8123 of this embodiment is connected to an end away from the nut, of the first locking bolt 8122, and the first locking bolt 8122 can rotate about its own axis on the first clamping arm 8123, so that the first locking bolt 8122 can drive the first clamping arm 8123 of the embodiment to move by rotating in the screw hole of the embodiment.

The pressing assembly 8124 of this embodiment is installed on the side away from the mounting base 8121, of the first clamping arm 8123. The second clamping arm 8125 is arranged opposite to the first clamping arm 8123 of this embodiment. The pressing component 8124 and the second clamping arm 8125 can jointly clamp the second rotating device 630, and the distance between the two is adjustable to adapt to the second rotating device 630 of different sizes, improving adaptability.

Optionally, in this embodiment, the pressing assembly 8124 is designed to include a first slider 81241, a second slider 81242, a first connecting rod 81243, a second connecting rod 81244, a third connecting rod 81245, a fourth connecting rod 81246, a first compression block 81247 and a second compression block 81248. Correspondingly, in this embodiment, a first slide groove 81231 and a second slide groove 81232 are provided on the side away from the mounting base 8121, of the first clamping arm 8123.

In this embodiment, the first slider 81241 is installed in the first slide groove 81231, the second slider 81242 is installed in the second slide groove 81232, and the first slider 81241 and the second slider 81242 can slide back and forth along the length direction of the first clamping arm 8123 in the corresponding slide groove. In this embodiment, the sides of the first pressing block 81247 and the second pressing block 81248 facing the second clamping arm 8125 have arc surfaces. In this embodiment, one end of the first connecting rod 81243 is hinged to the first slider 81241, and the other end is hinged to the first pressing block 81247. One end of the second connecting rod 81244 is hinged to the second slider 81242, and the other end is also hinged to the first pressing block 81242. One end of the third connecting rod 81245 of this embodiment is hinged to the second slider 81242 of this embodiment, and the other end is hinged to the first clamping arm 8123 of this embodiment.

The first pressing block 81247 and the second pressing block 81248 can rotate to a certain extent during pressing through the above-mentioned connecting rod structure. Moreover, since both the first pressing block 81247 and the second pressing block 81248 have arc surfaces, when encountering the clamped surface of the second rotating device 630 is not flat, good clamping and fixation of the second rotating device 630 between the pressing assembly 8124 and the second clamping arm 8125 can also be achieved.

Similarly, the structure of the second connection mechanism 813 of this embodiment can also be the same as that of the first connection mechanism. Therefore, the specific structural form of the second connection mechanism 813 of this embodiment will not be described too much in this embodiment.

When it is necessary to assemble the wire harness unit 800 to the second rotating device 630 of the movement unit 600, first placing the part of the second rotating device 630 between the first clamping arm 8123 and the second clamping arm 8125 of the first connection mechanism 812, and then operating the first locking bolt 8122 of this embodiment to compress the pressing assembly 8124 of the first connection mechanism 812 and the second clamping arm 8125. In the same way, the second connection mechanism 813 is operated to complete the connection and fixation of the wire harness unit 800 and the second rotating device 630.

Considering that the motion of the movement unit 600 has three dimensions, the motion of the cable 1100 is also multi-dimensional. Therefore, the ordinary structure for fixing and binding the cable 1100 may not be able to meet the motion requirements of the cable 1100, especially after the cable 1100 is fixed by the existing wire harness, when the fixed movable length of the cable 1100 is longer, it is still unavoidable that the cable 1100 enters the sterile operation area. When the fixed movable length of the cable 1100 is shorter, the cable 1100 is easily stretched, thereby causing damage to the cable 1100. Therefore, this embodiment provides a wire harness structure with adjustable beam length.

Figure 9:
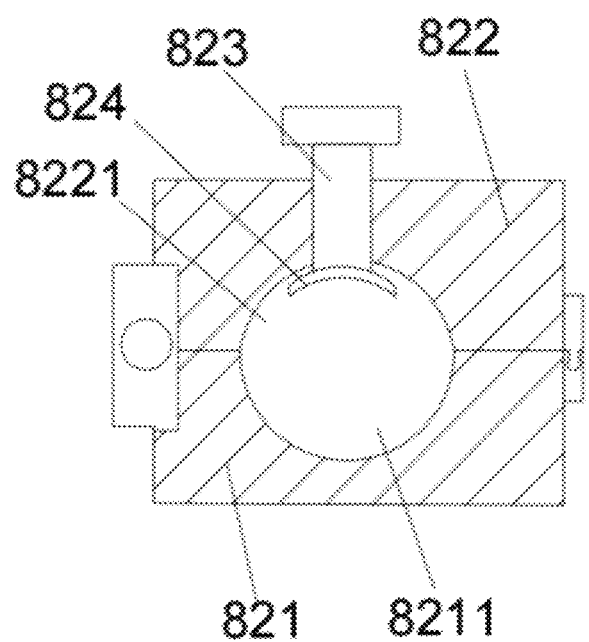
FIG. 9 is a schematic structural diagram of the first wire harness device of the C-arm machine provided by another embodiment of the present disclosure.

As shown in FIG. 8 and FIG. 9, the first wire harness device 820 of this embodiment includes a first wire harness seat 821, a second wire harness seat 822, a second locking bolt 823 and a pressing member 824. The first wire harness seat 821 of this embodiment is installed on the first mounting plate 811, and the first wire harness seat 821 is provided with a first arc-shaped groove 8211. One end of the second wire harness seat 822 in this embodiment is hinged to one end of the first wire harness seat 821 in this embodiment, and the other end is snap-fitted with the first wire harness seat 821. A side facing the first wire harness seat 821, of the second wire harness seat 822 is provided with a second arc-shaped groove 8221. A screw hole is provided in the middle of the second wire harness seat 822 in this embodiment.

The second locking bolt 823 of this embodiment is installed in the screw hole of the second wire harness seat 822 and is located in the second arc-shaped groove 8221. One end of the second locking bolt 823 in the second arc-shaped groove 8221 is installed with the pressing member 824 of this embodiment. The pressing member 824 may have an arc-shaped structure. When it is necessary to fix the cable 1100, contacting the snap fit of the first wire harness seat 821 and the second wire harness seat 822, putting the cable 1100 into the snap fit, and then fastening the first wire harness seat 821 and the second wire harness seat 822, one end of the first wire harness seat 821 and the second wire harness seat 822 is clamped and the other end of the first wire harness seat 821 and the second wire harness seat 822 is hinged, and finally screwing the second locking bolt 823, so that the pressing member 824 of this embodiment locks the cable 1100 in the first arc-shaped groove 8211 and the second arc-shaped groove 8221.

As shown in FIG. 8, the second wire harness device 830 of this embodiment includes a sliding plate 831, an elastic member 832, a first wire harness pulley 833, a second wire harness pulley 834, a third wire harness pulley 835, a first rotating shaft 836, a first damping rotating shaft 837 and the second damping rotating shaft 838. Correspondingly, in this embodiment, a third slide groove 8111 is provided on the first mounting plate 811, and the sliding plate 831 is slidably installed in a direction that is close to or far away from the first wire harness device 820 of this embodiment, in the third slide groove 8111. The elastic member 832 of this embodiment is connected to the third slide groove 8111 and the sliding plate 831 of this embodiment respectively.

The first wire harness pulley 833, the second wire harness pulley 834 and the third wire harness pulley 835 of this embodiment are all provided with approximately V-shaped wire grooves. The first wire harness pulley 833 of this embodiment is rotatably installed on the sliding plate 831 through the first rotating shaft 836. The second wire harness pulley 834 of this embodiment is rotatably installed on the sliding plate 831 of this embodiment through the first damping rotating shaft 837. The third wire harness pulley 835 of this embodiment is rotatably installed on the sliding plate 831 of this embodiment through the second damping rotating shaft 838.

When the cable 1100 is located between the second wire harness pulley 834 and the third wire harness pulley 835, the second wire harness pulley 834 and the third wire harness pulley 835 can compress the cable 1100, and due to the first damping rotating shaft 837 and the second damping rotating shaft 838, the cable 1100 can be fixed without being affected by external force.

Moreover, the distance between the second wire harness pulley 834 and the third wire harness pulley 835 in this embodiment is designed to be adjustable, for example, a number of evenly spaced slots (not shown in the figure) are provided at the bottom of the sliding plate 831. The bottom of the first damping rotating shaft 837 is provided with a plug connector that matches the slots. By adjusting the fit of the plug connector with different slots, the distance between the second wire harness pulley 834 and the third wire harness pulley 835 can be adjusted, so as to install the cable 1100 conveniently.

When the cable 1100 is bundled, it is first fixed through the first wire harness device 820 of this embodiment, and then the cable 1100 is sleeved on the first wire harness pulley 833 of this embodiment, and distance between the second wire pulley 834 and the third wire harness pulley 835 is enlarged, the cable 1100 is placed between the second wire harness pulley 834 and the third wire harness pulley 835, and then the second wire harness pulley 834 and the third wire harness pulley 835 are adjusted to be close to each other, thereby realizing the limitation of the cable 1100.

Using this type of wire harness unit 800, the cable 1100 is fixed through the first wire harness device 820, and the movable length of the cable 1100 can be effectively shortened through adjustment of the distance between the second wire harness device 830 and the first wire harness device 820, to bundle the cable 1100. Moreover, when the cable 1100 moves too much and movable part thereof is small, under the pulling force of the cable 1100, the sliding plate 831 of the second wire harness device 830 of this embodiment moves closer to the first wire harness device 820. At this time, the elastic member 832 is compressed. Since the first wire harness pulley 833, the second wire harness pulley 834, and the third wire harness pulley 835 cannot completely fix the cable 1100, the cable 1100 can move between the three wire harness pulleys. At this time, since the distance between the first wire harness device 820 and the second wire harness device 830 is reduced, the movable length of the cable 1100 is increased, thus allowing the cable 1100 to continue to move.

When the cable 1100 is reset after the above action, the movable part of the cable 1100 becomes longer. At this time, no pulling force is given to the sliding plate 831, so the elastic member 832 can drive the sliding plate 831 to reset under its own elastic restoring force. This further increases the distance between the first wire harness device 820 and the second wire harness device 830 to reduce the movable part of the cable 1100 and prevent the cable 1100 from intruding into the sterile operating area.

The above descriptions are only preferred embodiments of the present disclosure. Those skilled in the art should understand that the disclosure scope involved in the present disclosure is not limited to technical solutions formed by a specific combination of the above technical features, but should also cover any solution consisting of the above technical features or other technical solutions formed by any combination of equivalent features, without departing from the above disclosed concept. For example, a technical solution is formed by replacing the above features with technical features with similar functions disclosed in the present disclosure (but not limited to).

What is claimed is:

1. An intelligent planning method for puncture path in PVP surgery, comprising:

intercepting a local CT image of a complete spinal vertebral body from an original spine CT image;

identifying a midpoint of a narrowest part of left and right vertebral pedicles and left and right theoretical puncture injection stop-points of the spinal vertebral body, from the local CT image of the complete spinal vertebral body through a trained neural network model, the left and right theoretical puncture injection stop-points are optimal puncture injection stop-points without considering a leakage of bone cement;

calculating a distance $D_1$ from any of the left and right theoretical puncture injection stop-points in the local CT image of the complete vertebral body to a middle plane in a front-back direction of the vertebral body, a distance $D_2$ from the any of the left and right theoretical puncture injection stop-points to a middle plane in a left-right direction of the vertebral body, and a shortest distance $D_3$ from the any of the left and right theoretical puncture injection stop-points to a surface of a cortical bone of the vertebral body, taking a minimum value of the distance $D_1$, the distance $D_2$, and the distance $D_3$ as a radius of a space sphere area with the any of the left and right theoretical puncture injection stop-points as a sphere center; determining a radius of another space sphere area with the other one of the left and right theoretical puncture injection stop-points as a sphere center according to a way of aforementioned determination of the radius of the space sphere area with the any of the left and right theoretical puncture injection stop-points as the sphere center;

using a line connecting a midpoint of a narrowest part of any vertebral pedicle and any point in the space sphere area with a one of the left and right theoretical puncture injection stop-points as a sphere center, as an optional puncture path for the spinal vertebral body; wherein the one of the left and right theoretical puncture injection stop-points and the midpoint are at a same side;

sampling coordinate points in the space sphere area with the left and right theoretical puncture injection stop-points as the sphere center according to a preset sampling step, to obtain multiple candidate puncture injection stop-points;

calculating a value of a comprehensive distance D corresponding to each of the candidate puncture injection stop-points:

$$D = \frac{D_1 + D_4 + D_5}{D_6}$$

wherein $D_4$ represents a minimum distance between the candidate puncture injection stop-points and a fracture surface, and $D_5$ represents a minimum distance between the candidate puncture injection stop-points and a fracture line, $D_6$ represents a minimum distance between the candidate puncture injection stop-points and the left and right theoretical puncture injection stop-points;

using a candidate puncture injection stop-point with a largest comprehensive distance D as the optimal puncture injection stop-point in response to the leakage of bone cement being considered, and using a line connecting the midpoint of the narrowest part of the vertebral pedicle to the optimal puncture injection stop-point as the optimal puncture path in response to the leakage of bone cement being considered.

2. The intelligent planning method for puncture path in PVP surgery according to claim 1, further comprises:

marking the midpoints of the narrowest points of the left and right vertebral pedicles and the left and right theoretical puncture injection stop-points of the spinal vertebral body, in samples of the local CT image of multiple complete spinal vertebral body;

training a neural network model by using the marked samples of the local CT image to obtain the trained neural network model.

3. The intelligent planning method for puncture path in PVP surgery according to claim 1, wherein the neural network model is an SPU-Net network model.

4. An electronic device, comprising:

one or more processors;

a memory configured to store one or more programs;

when the one or more programs are executed by the one or more processors, the one or more processors are caused to implement an intelligent planning method for puncture path in PVP surgery comprising:

intelligent planning method for puncture path in PVP surgery, comprising:

intercepting a local CT image of a complete spinal vertebral body from an original spine CT image;

identifying a midpoint of a narrowest part of left and right vertebral pedicles and left and right theoretical puncture injection stop-points of the spinal vertebral body, from the local CT image of the complete spinal vertebral body through a trained neural network model, the left and right theoretical puncture injection stop-points are optimal puncture injection stop-points without considering a leakage of bone cement;

calculating a distance $D_1$ from any of the left and right theoretical puncture injection stop-points in the local CT image of the complete vertebral body to a middle plane in a front-back direction of the vertebral body, a distance $D_2$ from the any of the left and right theoretical puncture injection stop-points to a middle plane in a left-right direction of the vertebral body, and a shortest distance $D_3$ from the any of the left and right theoretical puncture injection stop-points to a surface of a cortical bone of the vertebral body, taking a minimum value of the distance $D_1$, the distance $D_2$, and the distance $D_3$ as a radius of a space sphere area with the any of the left and right theoretical puncture injection stop-points as a sphere center; determining a radius of another space sphere area with the other one of the left and right theoretical puncture injection stop-points as a sphere center according to a way of aforementioned determination of the radius of the space sphere area with the any of the left and right theoretical puncture injection stop-points as the sphere center;

using a line connecting a midpoint of a narrowest part of any vertebral pedicle and any point in the space sphere area with one of the left and right theoretical puncture injection stop-points as a sphere center, as an optional puncture path for the spinal vertebral body; wherein the one of the left and right theoretical puncture injection stop-points and the midpoint are at a same side;

sampling coordinate points in the space sphere area with the left and right theoretical puncture injection stop-points as the sphere center according to a preset sampling step, to obtain multiple candidate puncture injection stop-points;

calculating a value of a comprehensive distance D corresponding to each of the candidate puncture injection stop-points:

$$D = \frac{D_1 + D_4 + D_5}{D_6}$$

wherein $D_4$ represents a minimum distance between the candidate puncture injection stop-points and a fracture surface, and $D_5$ represents a minimum distance between the candidate puncture injection stop-points and a fracture line, $D_6$ represents a minimum distance between the candidate puncture injection stop-points and the left and right theoretical puncture injection stop-points;

using a candidate puncture injection stop-point with a largest comprehensive distance D as the optimal puncture injection stop-point in response to the leakage of bone cement being considered, and using a line connecting the midpoint of the narrowest part of the vertebral pedicle to the optimal puncture injection stop-point as the optimal puncture path in response to the leakage of bone cement being considered.

5. The electronic device according to claim 4, wherein:
when the one or more programs are executed by the one or more processors, the one or more processors are further caused to implement the intelligent planning method for puncture path in PVP surgery comprising:
marking the midpoints of the narrowest points of the left and right vertebral pedicles and the left and right theoretical puncture injection stop-points of the spinal vertebral body, in samples of the local CT image of multiple complete spinal vertebral body;
training a neural network model by using the marked samples of the local CT image to obtain the trained neural network model.

6. The electronic device according to claim 4, wherein the neural network model is an SPU-Net network model.

7. A non-transitory computer-readable storage medium, on which a computer program is stored, wherein when the computer program is executed by a processor, the intelligent planning method for puncture paths in PVP surgery as described in claim 1 is implemented.

8. A non-transitory computer-readable storage medium, on which a computer program is stored, wherein when the computer program is executed by a processor, the intelligent planning method for puncture paths in PVP surgery as described in claim 2 is implemented.

9. A non-transitory computer-readable storage medium, on which a computer program is stored, wherein when the computer program is executed by a processor, the intelligent planning method for puncture paths in PVP surgery as described in claim 3 is implemented.

* * * * *